United States Patent [19]

Schumann

[11] Patent Number: Plant 5,940

[45] Date of Patent: Apr. 14, 1987

[54] GERANIUM PLANT NAMED VOLCANO

[75] Inventor: Ingeborg Schumann, Bad Ems, Fed. Rep. of Germany

[73] Assignee: Fischer Geraniums, Inc., Netherlands Antilles

[21] Appl. No.: 761,099

[22] Filed: Jul. 31, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A geranium plant named Volcano having red flower color; semi-double to single flower form; good rooting; compact growth habit; good chlorophyll quality for transportation; and good temperature tolerance.

1 Drawing Figure

1

The present invention comprises a new and distinct cultivar of geranium, botanically known as *Pelargonium zonale,* and hereinafter referred to by the cultivar name Volcano.

Volcano is a product of a planned breeding program which had the objective of creating new geranium cultivars having red flower color, semi-double flower form, good chlorophyll quality for shipping, good rooting, temperature tolerance and compact growth habit.

Volcano was originated from a hybridization made by Ingeborg Schumann in a controlled breeding program in Hillscheid, Federal Republic of Germany in 1979. The female parent was an inbred line of Vesuv. The male parent of Volcan was an inbred line of Rubin. Both parents are unpatented.

Volcano was discovered and selected as one flowering plant within the progeny of the stated cross by Ingeborg Schumann in July of 1980 in a controlled environment in Hillscheid, Federal Republic of Germany.

The first act of asexual reproduction of Volcano was accomplished when vegetative cuttings were taken from the initial selection in January of 1981 in a controlled environment in Hillscheid, Federal Republic of Germany by a technician working under formulations established and supervised by Ingeborg Schumann. Horticultural examination of selected units initiated in the spring of 1981 and continuing in 1982 and 1983 has demonstrated that the combination of characteristics as herein disclosed for Volcano are firmly fixed and are retained through successive generations of asexual reproduction.

Volcano has not been observed under all possible environmental conditions. The phenotype may vary significantly with variations in environment such as temperature, light intensity, and day length. The following observations, measurements and comparisons describe plants grown in Hillscheid, Federal Republic of Germany, under conditions which approximate those generally used in commercial practice.

The following traits have been repeatedly observed and are determined to be basic characteristics of Volcano, which in combination distinguish this geranium as a new and distinct cultivar.

1. Red flower color.
2. Semi-double to single flower form.
3. Compact growth habit.
4. Good chlorophyll quality for transportation.

2

5. Good rooting.
6. Excellent self branching.
7. Good temperature tolerance.

Of the many commercial cultivars known to the present inventor, perhaps the most similar in comparison to Volcano is Vesuv. Reference is made to the attached Chart A which compares certain characteristics of Volcano to those same characteristics of Vesuv, and also to the same characteristics of Rubin and Mars. Mars is disclosed in U.S. Plant Pat. No. 5,372, and Rubin was a commercial variety of Pelargonien-Fischer KG, Hillscheid, Federal Republic of Germany. In comparison to Vesuv, Volcano has a brighter red color, a better chlorophyll quality for transportion, a longer peduncle length, and a larger flowerhead. When compared to Rubin and Mars, Volcano is a much brighter red.

The accompanying photographic drawing shows typical flower and foliage characteristics of Volcano, with colors being as true as possible with illustrations of this type.

In the following description color references are made to The Royal Horticultural Society Colour Chart. The color values were determined between 11:00 a.m. and 12:00 noon on May 22, 1985 under 40,000 Lux light intensity at Hillscheid, Federal Republic of Germany.

Classification:

*Botanical.*—A hybrid of the genus Pelargonium l'hert and species *Pelargonium zonale.*

*Commercial.*—Volcano.

INFLORESCENCE

A. Umbel:

*Average diameter.*—114 mm.

*Average depth.*—72 mm.

*Peduncle length.*—210 mm.

*Pedicel length.*—32 mm.

B. Corolla:

*Average diameter.*—51 mm.

*Form.*—Semi-double to single; round.

*Color (general tonality from a distance of three meters).*—Red. Upper surface: 43A.

C. Bud:

*Shape.*—Oval; flat top.

*Color.*—Red.

D. Reproductive organs:

*Androecium.*—Mostly sterile; sometimes 5 to 8 stamens.

*Gynoecium.*—4–5 lobed stigma.

E. Spring flowering response period: In Hillscheid, Federal Republic of Germany, in 1982, 70% of plants opened with at least one flower 13 weeks after planting of unrooted cuttings.

F. Outdoor flower production: The total flower count in 1982 in Hillscheid, Federal Republic of Germany, was between 55 and 58 flowers per plant for the June through October observation period.

G. Durability: Good.

PLANT

A. Foliage:

*Form.*—Kidney shaped.

*Margin.*—Rounded, wavy, crenate.

*Color.*—Top surface: Medium green, 137B–C. Zonation: Weak.

*Tolerance of botrytis.*—Good.

B. General appearance and form:

*Internode length.*—25 mm.

*Branching pattern.*—3.8 branches per plant.

*Height.*—230 mm.

CHART A

| CULTIVAR | COROLLA COLOR | PEDUNCLE LENGTH | UMBEL AVERAGE |
|---|---|---|---|
| Volcano | RHS 43A | 210 mm | 114 mm |
| Vesuv | RHS 43B | 200 mm | 109 mm |
| Rubin | RHS 33A | 213 mm | 108 mm |
| Mars | RHS 33A | 221 mm | 109 mm |

| CULTIVAR | BRANCHING HABIT | EARLY FLOWER RESPONSE (% of plants in flower after 13 weeks) | INTERNODE LENGTH |
|---|---|---|---|
| Volcano | 3.8 | 70% | 25 mm |
| Vesuv | 3.0 | 50% | 23 mm |
| Rubin | 2.8 | 75% | 31 mm |
| Mars | 7.4 | 75% | 31 mm |

I claim:

1. A new and distinct cultivar of geranium named Volcano, as described and illustrated, and particularly characterized by its red flower color; semi-double to single flower form; good rooting; compact growth habit; good chlorophyll quality for transportation; and good temperature tolerance.

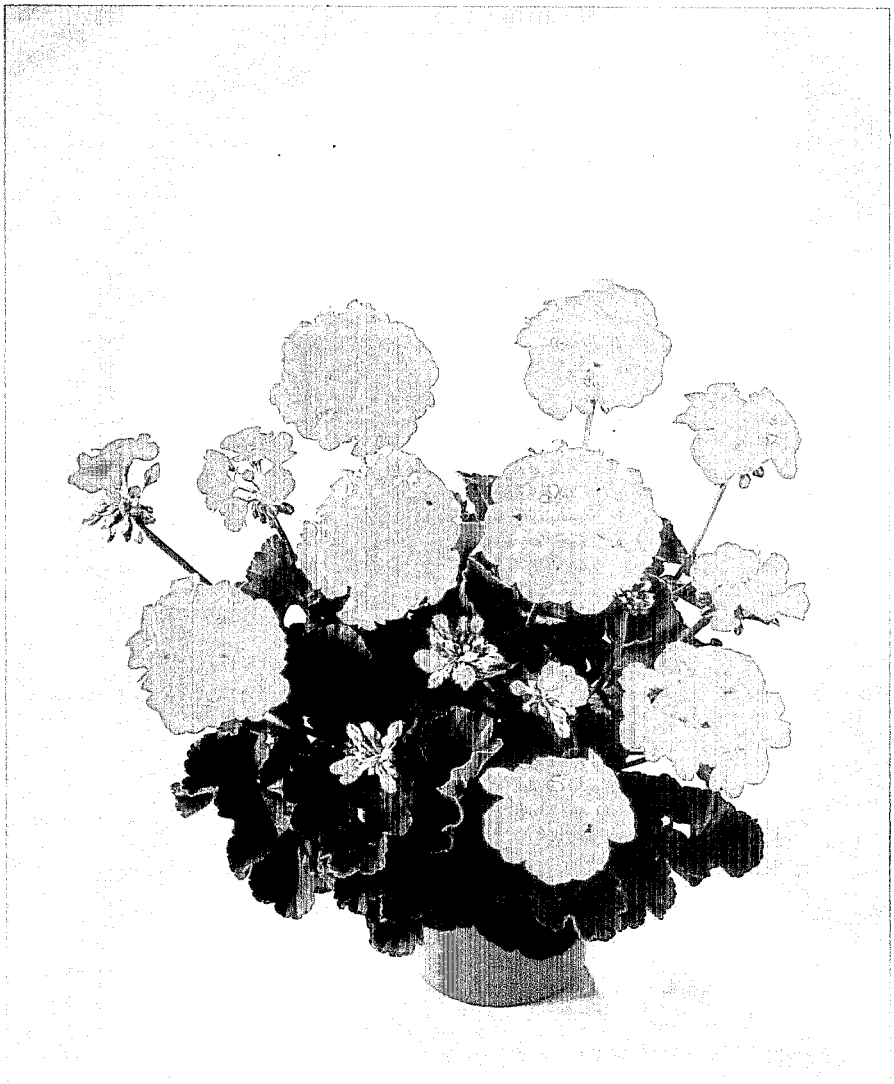

* * * * *